US012697461B2

(12) United States Patent (10) Patent No.: US 12,697,461 B2

Bolier et al. (45) Date of Patent: Aug. 4, 2026

(54) RELAXATION DEVICE WITH BREATHING MOTION SIMULATOR

(71) Applicant: Somnox Holding B.V., Rotterdam (NL)

(72) Inventors: Lucas Jan Bolier, Rotterdam (NL); Stijn Jeroen Antonisse, Rotterdam (NL)

(73) Assignee: Somnox Holding B.V., Rotterdam (NL)

( * ) Notice: Subject to any disclaimer, the term of this patent is extended or adjusted under 35 U.S.C. 154(b) by 1184 days.

(21) Appl. No.: 17/679,323

(22) Filed: Feb. 24, 2022

(65) Prior Publication Data

US 2022/0265958 A1 Aug. 25, 2022

(30) Foreign Application Priority Data

Feb. 25, 2021 (NL) ...................................... 2027643

(51) Int. Cl.
A61M 21/02 (2006.01)
A61M 21/00 (2006.01)
A63H 3/00 (2006.01)

(52) U.S. Cl.
CPC ............. A61M 21/02 (2013.01); A63H 3/001 (2013.01); A61M 2021/0022 (2013.01);
(Continued)

(58) Field of Classification Search
CPC .......... A61M 21/02; A61M 2021/0022; A61M 2021/0027; A61M 2021/0061; A61M 2021/0088; A63H 3/001; G09B 23/288
See application file for complete search history.

(56) References Cited

U.S. PATENT DOCUMENTS 3,110,980 A * 11/1963 Moormann ............ A63H 3/001
446/295
4,606,328 A * 8/1986 Thoman ................ A63H 3/001
446/295
(Continued)

FOREIGN PATENT DOCUMENTS

CA 3128877 A1 * 8/2020 ............. A61B 5/082
WO WO-2018127262 A1 * 7/2018 ............. G09B 23/28
(Continued)

OTHER PUBLICATIONS

Gunn, K. (Dec. 18, 2012). Creating living hinges—make:. Make: https://makezine.com/projects/creating-living-hinges/ (Year: 2012).*
(Continued)

*Primary Examiner* — Alex M Valvis
*Assistant Examiner* — Julie Thi Tran
(74) *Attorney, Agent, or Firm* — Hoffmann & Baron, LLP

(57) ABSTRACT

A breathing motion simulator for simulating an expanding and retracting movement of live breathing, includes a pump and an inflatable bladder for generating a repetitive motion resembling a breathing motion. The simulator includes a cover plate positioned across the bladder and a cover guidance for linearly guiding the cover plate with respect to a base body. The cover guidance includes at least a first living hinge unit and a second living hinge unit oriented in a non-parallel direction with respect to each other for constraining a rotational movement of the cover plate, where each living hinge unit includes at least three stacked living hinges defining a set of three pivot axes in parallel for allowing a translational movement of the cover plate, such that the cover guidance enables a linear movement of the cover plate.

20 Claims, 7 Drawing Sheets

(52) U.S. Cl.
CPC ............... *A61M 2021/0027* (2013.01); *A61M*
*2021/0061* (2013.01); *A61M 2021/0088*
(2013.01)

(56) References Cited

U.S. PATENT DOCUMENTS

| | | | |
|---|---|---|---|
| 4,718,876 A * | 1/1988 | Lee ........................ | A63H 3/001 |
| | | | 601/78 |
| 4,932,879 A * | 6/1990 | Ingenito ............... | G09B 23/288 |
| | | | 273/460 |
| 5,613,892 A * | 3/1997 | Barton ..................... | A63H 3/06 |
| | | | 446/224 |
| 2005/0058977 A1* | 3/2005 | Cantrell ............... | G09B 23/288 |
| | | | 434/350 |
| 2010/0229875 A1 | 9/2010 | Davis | |
| 2011/0056502 A1 | 3/2011 | Davis et al. | |
| 2011/0301405 A1 | 12/2011 | Cho | |
| 2015/0125840 A1* | 5/2015 | Pastrick ............... | G09B 23/288 |
| | | | 53/474 |
| 2019/0117929 A1* | 4/2019 | Reinberg ............ | B23D 45/105 |

FOREIGN PATENT DOCUMENTS

| | | | | |
|---|---|---|---|---|
| WO | 2020/162750 A1 | 8/2020 | | |
| WO | WO-2022032033 A1 * | 2/2022 | ........... | G09B 23/288 |

OTHER PUBLICATIONS

NL Search Report, Application No. 2027643, Feb. 25, 2021, 7 pages.

* cited by examiner

RELAXATION DEVICE WITH BREATHING MOTION SIMULATOR

This application is a U.S. application claiming priority to and the benefit of Netherlands application NL2027643, the entire contents of which are incorporated by reference.

FIELD OF TECHNOLOGY

The present invention relates to a breathing motion simulator, e.g. in the form of a pillow or a toy doll, comprising an actuator, e.g. a pump and a bladder, a cover plate and a cover guidance. In particular, the invention relates to a relaxation device for relaxing a user, in particular for inducing sleep, a so-called sleep inducer, comprising such a breathing motion simulator.

BACKGROUND

WO2020/162750 in the name of the same applicant discloses a haptic respiration simulator for relaxing a user by simulating a respiration. The simulator is formed by a pillow which is to be held close to the users body. The stimulator has a housing which is surrounded by a soft layer of a foam material forming an outer soft skin. The simulated respiration is sensible by a user by touching the stimulator, e.g. by placing a hand on a hand pad of the stimulator. An inflatable air chamber is positioned at an outer surface of the housing and configured to simulate a respiration by repeated inflation and deflation of the inflatable air chamber. This inflation and deflation of the inflatable air chamber can be commenced by a user through the outer skin of the simulator.

U.S. Pat. No. 4,606,328 discloses a toy animal which is arranged to simulate a naturally breathing motion. The toy animal is to be laid in a crib within a vestibulary (motion sensing) and tactile (touch) vicinity of a child to comfort it during sleep or rest periods. The toy animal has a trunk with a back portion which includes a stiff section. The bladder is firmly attached to the stiff section. The stiff section forms an anchor for an expandable bladder. It is mentioned that the bladder also enclosed in a pleural cavity of the toy animal, it is thereby possible to simulate actual breathing motions of a live animal, including the natural extension-contraction of the pleural cavity. Significant motion of an outer surface of the trunk is obtained.

US2011/0301405 discloses a device for inducing sleep, a sleep inducer, comprising a cover and a moving plate included inside the cover and disposed underneath the cover. The cover is made of a flexible material to easily transmit motion of the moving plate to the outside. Moving means are provided to repeatedly and vertically moving the moving plate. The vertical movement of the moving plate can raise a part or an entire area of the cover positioned thereon. The vertical movement is in particular in a range of a gap of 0.1 cm to 5.0 cm. The moving means may include a piston connected to a bottom surface of the moving plate. Alternatively, the moving means may include a foldable tube that is shrunk and expanded underneath the moving plate by a supply and discharge of air. In between the cover and the moving plate, the sleep inducer may include a pad capable of shrinking and expanding formed between the cover and the moving plate to allow evenly transmitting movement to an entire area of the cover mounted on the moving plate.

WO2018/127262 discloses a training manikin for practising cardiopulmonary resuscitation. The manikin has a torso part. The torso part comprises a base board, a chest board with a male part and a lung plate with a matching female part. The male and female parts being adapted to guide a displacement of approximately 5-7 cm of said chest board relative to the lung plate. A lung bag is positioned in between the chest board and the lung plate. The lung bag is attached to the lung plate by an adhesive. The male part formed by a protrusion on the chest board penetrates an opening of the lung plate forming the female part. In an assembly of the torso plate, the penetration of the male and female parts ensure a correct positioning of the lung bag during use. A flexible side wall is provided along an entire circumference of the chest board to permanently connect the chest board and a base board.

A drawback to known breathing motion simulators is that each one produces less or more operational noise during operation. This operational noise which may originate from different movable components, like the pump, bladder and cover guidance, is especially cumbersome in a device like a relaxing device which is designed to be used under quiet circumstances.

The general object of the present invention is to at least partially eliminate the above mentioned drawback and/or to provide a usable alternative. More specifically, it is an object of the invention to provide a breathing motion simulator which is more silent in operation. In particular, it is an object of the invention to provide a relaxation device including such a silent breathing motion simulator.

SUMMARY OF THE INVENTION

According to the invention, this object is achieved by a breathing motion simulator according to the present invention.

In a first aspect, according to the invention, a breathing motion simulator for simulating an expanding and retracting movement of a breathing is provided.

The breathing motion simulator comprises an actuator system for generating a motion. The motion of a repetitive expanding and retracting resembles a breathing motion, a live breathing, in particular a natural breathing motion of a human being. In particular the actuator system comprises an inflatable bladder for generating a motion resembling a breathing motion and a pump unit including a pump for supplying a fluid to the bladder, in which the pump is in fluid communication with the bladder.

The breathing motion simulator comprises a cover plate. The cover plate has an outer surface which is sized to move a predetermined area of a device, e.g. a side region of a relaxation device. The actuator system is connected to the cover plate to induce the motion to the cover plate.

The breathing motion simulator comprises a cover guidance for linearly guiding the cover plate with respect to a base body. Particularly, the cover guidance is arranged for guiding the cover plate in a direction in perpendicular with the base body. The cover plate is connected to an upper portion of the cover guidance. A lower portion of the cover guidance is connectable to the base body.

The breathing motion simulator according to the invention is improved in that the cover guidance comprises at least a first living hinge unit and a second living hinge unit oriented in a non-parallel direction with respect other. Preferably, the first and second living hinge unit have a same configuration. In particular, the first and second living hinge unit are oriented in a perpendicular direction with respect to each other. Preferably, the first and second living hinge unit are positioned along a circumference of the cover plate. The non-parallel orientation provide a rotational constraint to the connected cover plate. Due to the orientation a rotational movement of the cover plate is prevented, whilst a translational movement away from the base body is allowed.

Each living hinge unit of the cover guidance comprises at least three stacked living hinges. The living hinges are situated above each other. The first living hinge is positioned at the lower portion of the cover guidance. The second living hinge is positioned in between the first and third living hinge which third living hinge is in case of three living hinges positioned at the upper portion of the cover guidance. Each living hinge defines a pivot axis in a longitudinal direction. The living hinges of each living hinge unit are directed in the same direction. The at least three stacked living hinges define a set of at least three pivot axes which extend in parallel with each other. This arrangement of the stacked living hinges allows a translational movement of the cover plate. In the translational movement, the second and third living hinge are movable away from the first living hinge at the lower portion of the cover guidance. The living hinge at the upper portion moves away from the first living hinge. Herewith, the cover guidance provides a guidance to the cover plate in which a linear movement of the cover plate is secured.

The breathing motion simulator according to the invention may provide several benefits.

The presence of the cover guidance in which only a single degree of freedom DOF, a movement in translation only, of the cover plate is permitted is an advantage in transferring a movement of an actuator underneath the cover plate to be sensed by a user at an outer side. The movement is best sensible by a user in a direction of movement perpendicular to the base body. The cover plate guided by the cover guidance in a unidirectional direction instead of an omnidirectional motion contributes to an improved sensibility of the repetitive motion.

The cover guidance is further beneficial, because the cover guidance allows an application of a smaller actuator, in particular a small bladder. As a repetitive motion of the bladder is transferred in a more effective way by the cover guidance, a relative smaller bladder can be used to obtain a same sensible breathing motion in comparison with a breathing motion simulator without such a cover guidance. A smaller bladder requires a smaller fluid volume to expand, such that a smaller pump may suffice. Smaller components contribute to a more compact and silent device.

The presence of the living hinge units provides an advantage in that these living hinge units can be manufactured as a one-piece item by injection moulding. Each living hinge of a living hinge unit is an integral item which is formed by a flexible section in between neighbouring rigid sections. Instead of a mounting of several parts to form a hinge, the integral form of the living hinge is beneficial in providing a freedom of movement, a rotational movement, without friction or sound produced by sliding parts. The application of living hinges which are silent in operation is a major advantage in an application of the breathing motion simulator in a device to be used as a relaxation device. The breathing motion simulator according to the invention which is improved in noise reduction is optimal to be used in a relaxation device for relaxing a user as such a relaxation device, e.g. a sleep inducer, is to be used in a silent environment, like a bedroom.

More in particular, the breathing motion simulator according to the invention is optimal to be used in a relaxation monitoring device which monitoring requires an even higher level of noise reduction than a more simple relaxation device. In the relaxation monitoring device a physiological characteristic of the user, e.g. a heart rate or a respiration frequency, is to be monitored. For accurate monitoring, the relaxation monitoring device is to be held close to the users body. For that reason of close proximity, the breathing motion simulator including the silent cover guidance is of a particular advantage in an application of a relaxation monitoring device.

The actuator system of the breathing motion simulator preferably comprises an inflatable bladder as an actuator and a pump unit as an actuator drive which may be beneficial in applying the breathing motion simulator in a relaxation device to reduce operational noise and vibrations. The pump unit includes a pump for supplying a fluid, in particular an airflow, to the bladder. The pump is in fluid communication connected with the bladder. Preferably, the cover plate is positioned across the bladder for covering the bladder, such that inflating the bladder generates a movement of the cover plate. The cover plate is movable together with the bladder to transfer the induced motion.

In an embodiment of the breathing motion simulator according to the invention, the cover guidance comprises a first, second and third living hinge unit. The third living hinge unit is oriented in parallel with the first living unit. Preferably, each living hinge unit is positioned along a circumference of the cover plate. In a view of projection, the cover plate may have a rectangular outer contour in which the first and third living hinge unit are positioned along a length direction of the cover plate. The second living hinge unit is positioned transversal, in particular perpendicular, to the first and third living hinge unit. The actuator is positioned in between the living hinge units. This embodiment may be beneficial to obtain a robust guidance of the cover plate in which the guidance is less vulnerable to possible deformations of the cover plate.

In an embodiment of the breathing motion simulator according to the invention, the cover guidance and/or cover plate are manufactured by injection moulding. The upper portion of the cover guidance may be connectable by a snap-connection to the cover plate to obtain a subassembly of the cover plate and cover guidance. Preferably, the cover guidance and cover plate are integrally formed as a one-piece item. The integrally shaped cover plate and cover guidance is beneficial in providing a sound reduction of the breathing motion simulator in operation.

In an embodiment of the breathing motion simulator according to the invention, the cover plate has an outer shape which is shaped in correspondence with a human hand palm. The cover plate is adapted to ergonomically receive a human hand for intuitively using a device including the breathing motion simulator.

In an embodiment of the breathing motion simulator according to the invention, the cover plate comprises a push body. The push body is adapted to be engaged by the actuator. The push body forms a protrusion extending away from an inner surface cover plate. The push body provides a predetermined location to be engaged by the actuator. The push body increases a rigidity of the cover plate at the location of engagement. Herewith, the push body contributes to a proper operation of the breathing motion simulator. Preferably, the push body is a hollow body formed by a plurality of wall portions. The wall portions may have a wall thickness allowing a manufacturing of push body by injection moulding. The push body and the cover plate may be integrally shaped by injection moulding. Alternatively, the push body may be a separate item to be assembled to the inner side of the cover plate. The push body may be connectable to the cover plate by at least one push body connector, in particular a push body snap connector.

In an embodiment of the breathing motion simulator according to the invention, the cover plate may be covered by a stretchable layer of material. The layer is stretchable to allow the cover plate to move with respect to the base plate. In particular, the stretchable layer is a foam layer. The stretchable layer biases the cover plate with respect to the base body. The stretchable layer encloses and attaches the cover plate to the base body to provide a pre-tension with respect to the base plate.

In an embodiment of the breathing motion simulator according to the invention, the stretchable layer is an at least partially open-worked layer. The layer has an open worked region which contributes to a lighter movement of the cover plate with respect to the base body which beneficially may reduce pump requirements. Advantageously, the open worked region may prevent a rupture of a foam layer. Preferably, the open worked region is laterally positioned with respect to the cover plate. The open worked region of the layer comprises at least one cut-out. The cut-out locally increases a flexibility of the layer. The cut-out may be formed by a plurality of apertures. Preferably, the cut-out includes at least one elongated groove. The elongated groove is directed potentially perpendicular to the linear motion of the cover plate. The elongated groove extends in a direction substantially in parallel with a living hinge of a living hinge unit which contributes to an increase stability in a direction of motion.

In an embodiment of the breathing motion simulator, the inflatable bladder is a permeable bladder, such that after an inflation, the bladder deflates due to a pre-tension on the cover plate e.g. provided by the stretchable layer. No active air suction is required for deflating the bladder. Beneficially, the permeable bladder allows a simple pump unit configuration.

Taken into account, the great benefits of the silently operating breathing motion simulator according to the invention in particular applications, the invention further relates to a relaxation device, in particular a sleep inducer, for influencing a relaxation of the user by providing a breathing motion simulation in which the relaxation device comprises a breathing motion simulator according to the invention. In particular, the invention relates to a relaxation monitoring device comprising a breathing motion simulator according to the invention. The relaxation monitoring device is an advanced relaxation device for influencing a relaxation of the user by providing a breathing motion simulation based on an input of a monitored physiological characteristic. The relaxation monitoring device comprises at least one sensor for monitoring a relaxation of the user. A control unit is configured to adapt a simulation of a breathing motion provided by the breathing motion simulator based on a received sensor signal from the at least one sensor. In use, the relaxation monitoring device is held in close proximity to a user's body in which the silent operation of the breathing motion simulator is especially beneficial. Besides other conceivable appliances, e.g. a manikin provided with a breathing motion simulator according to the invention, the silent operation of the breathing motion simulator according to the invention really means a considerable benefit in these relaxation devices for relaxing a person.

In an embodiment of the relaxation device according to the invention, the base body of the breathing motion simulator is formed by a housing in which the pump unit is housed inside an inner space of the housing and in which the cover guidance is connectable or connected to an outer surface of the housing. Preferably, the bladder is positioned by a form fit in between the cover plate and the housing. The cover guidance and cover plate may form a subassembly to be mounted across the bladder. In particular, the bladder of the breathing motion simulator is attached to the outer surface of the housing, e.g. by gluing.

In an embodiment of the relaxation device according to the invention, the cover plate of the breathing motion simulator extends in a length direction of the device, in particular from a head portion to a tail portion, about a distance of at least 30% of a total length of the device. Advantageously, the above described improved features of the cover guidance and/or the cover plate allow an application of a relatively large cover plate having a length of at least 8 cm.

Further, the invention relates to a method for providing a simulation of a breathing motion, wherein use is made of a breathing motion simulator according to the invention.

In a second aspect, according to the invention, a breathing motion simulator for simulating an expanding and retracting movement of a breathing is provided. The breathing motion simulator comprises an actuator system, e.g. an inflatable bladder with a pump unit or a piston assembly with a motorised link mechanism. The breathing motion simulator is configured for generating a motion of a repetitive expanding and retracting. The repetitive motion resembles a breathing motion, in particular a natural breathing motion of a human being.

The breathing motion simulator comprises a cover plate. The cover plate is positioned across an actuator for generating a motion of the actuator system. The cover plate is movable by the actuator.

The breathing motion simulator comprises a cover guidance for guiding the cover plate with respect to a base body. Particularly, the cover guidance is arranged for guiding the cover plate in a direction away from the base body. The cover plate is connected to an upper portion of the cover guidance. A lower portion of the cover guidance is connectable to the base body.

The breathing motion simulator according to the second aspect of the invention is improved in that the cover guidance comprises at least a first living hinge unit. The first living hinge unit comprises at least one living hinge. Preferably, the first living hinge unit is positioned along a circumference of the cover plate. The living hinge allows the cover plate to rotate with respect to the base body. The living hinge has a pivot axis which extends in a longitudinal direction substantially in parallel with an imaginary plane formed by the base body. Herewith, the cover plate is guided to move to and fro the base body.

According to the second aspect of the invention, the cover guidance including a living hinge provides an improvement in reducing operational noise of an apparatus. This is especially an advantage in an apparatus like a sleep inducer which is to be used in silent circumstances to allow user to relax.

In comparison with a guidance as disclosed in EP2243129B1 and EP1671299B1, the guiding of the cover plate according to the second aspect of the invention is improved by reducing an amount of separate parts. In contrast to a pivot including multiple parts, e.g. a pivot shaft and a pivot bearing, the living hinge can be formed as a one-piece item by injection molding. The living hinge is beneficial in reducing the amount of device components. The living hinge may reduce operational noise and friction. Another benefit is that the living hinge may contribute to a longer lifespan of the simulator as the living hinge may be less vulnerable to mechanical wear than a pivot out of multiple parts.

In an embodiment according to the second aspect of the breathing motion simulator, the cover plate has an outer shape which is shaped in correspondence with a human hand palm. The cover plate is adapted for receiving a human hand. Herewith, the breathing motion simulator is configured as a unit of a relaxation device, in particular a sleep inducer.

In an embodiment according to the second aspect of the breathing motion simulator, the cover guidance may comprise a first and second living hinge unit which are positioned opposite each other along an outer circumference of the cover plate. The cover plate comprises a first and second cover plate portion which are respectively connected by the first and second living hinge to the base body. The first and second cover plate portion are movable with respect to each other. The first and second cover plate portion may pivot or deviate from each other during operation. In particular, the first and second cover plate portion may slide with respect to each other. The cover plate may comprise a stretch portion in between the first and second cover plate portion to enable the deviation during operation.

In an embodiment, the actuator system of the breathing motion simulator comprises a pump unit. The pump unit includes a pump for supplying a fluid, in particular an airflow, to a bladder or a cylinder.

BRIEF DESCRIPTION OF THE DRAWINGS

The invention will be explained in more detail with reference to the appended drawings. The drawings show practical embodiments according to the invention, which may not be interpreted as limiting the scope of the invention. Specific features may also be considered apart from the shown embodiments and may be taken into account in a broader context as a delimiting feature, not only for the shown embodiment but as a common feature for all embodiments falling within the scope of the appended claims, in which:

DETAILED DESCRIPTION

Identical reference numbers or alternative prefixes are used in the following drawings to indicate the same or similar features.

Figure 1:
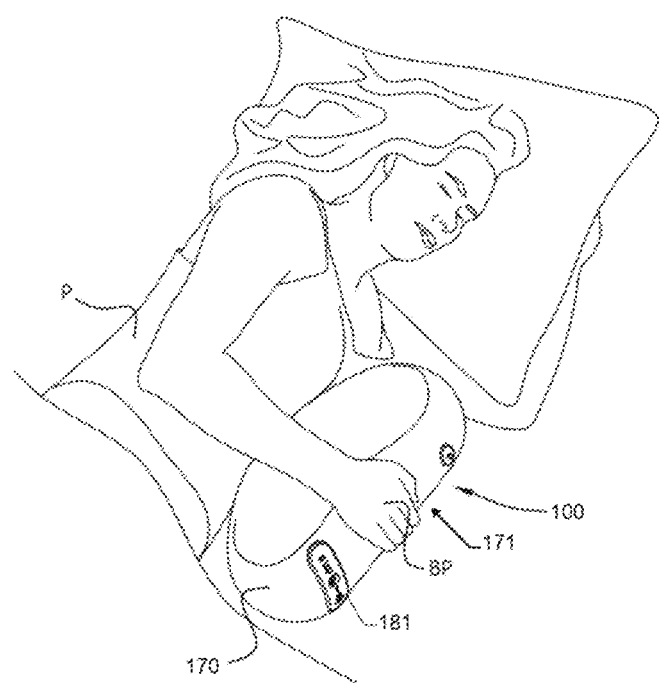
FIG. 1 schematically shows a user lying in bed while spooning and holding a relaxation device including a breathing motion simulator according to the invention.

FIG. 1 shows a person P who is relaxing in a bed. The person is lying on a side and an arm is resting on a relaxation device. The relaxation device is configured to provide successive stimuli to influence a breathing rhythm of the user by providing a haptic stimulus. The haptic stimulus resembles a breathing motion. The relaxation device is arranged to simulate a breathing motion to influence a relaxation of the user. The relaxation device can for example be used as a sleep inducer to help a user falling asleep.

Here, the relaxation device is a relaxation monitoring device 100 in which a generated haptic stimulus is adapted by a control unit based on a monitored physiological characteristic, e.g. a breathing frequency or a heart rate, of the user.

Here, the relaxation device is shaped as a hand-pillow. In the shown sleeping posture, a hand of the person is positioned at a hand pad of the relaxation monitoring device 100. The hand pad is configured for receiving a hand of the user. Here, the hand pad is formed by a concave portion of the hand pillow. The concave portion is dimensioned in correspondence with a human hand palm. The concave portion has a width which substantially equals a human hand width.

The hand pad is positioned in such a manner that the person may intuitively attract the relaxation monitoring device 100 close to the person's body which improves an accuracy of monitored characteristics and increases awareness of the provided stimuli. As shown, the person P and the relaxation monitoring device 100 are positioned in a so called spooning arrangement.

The relaxation monitoring device 100 has a cushion 170 at an outer side. The cushion 170 provides an outer soft skin. The cushion forms a cushioning support for a human body part BP, here a lower arm and hand. As further shown in FIG. 2, the cushion 170 includes a pillow-case 171 which is placed around a foam body 172. The pillow-case is of a textile material which is comfortable in skin contact and can be removed to be cleaned when desired.

Figure 2:
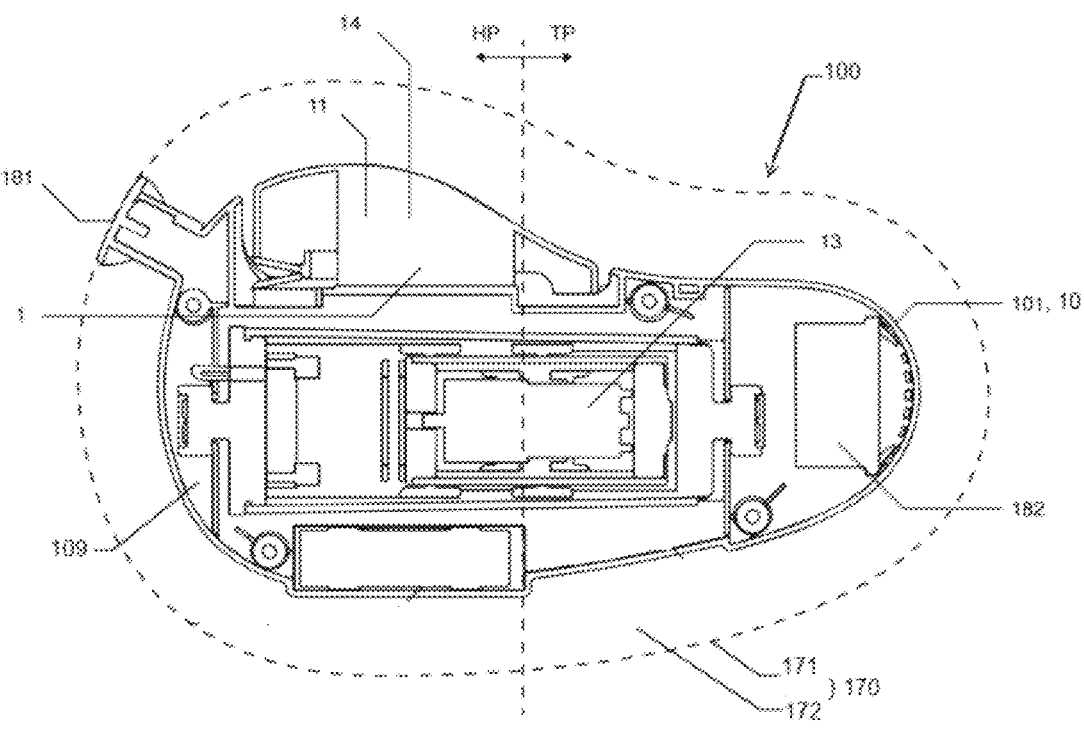
FIG. 2 shows a cross-sectional view in a longitudinal direction of a housing of the relaxation device of FIG. 1.

FIG. 2 shows a top view of the relaxation monitoring device 100 in which the cushion 170 is indicated by a dashed line. The relaxation monitoring device 100 has a housing 101 for housing components. The housing 101 comprises an outer shell which delimits an inner space 109 for containing the components, like a battery pack 190, a pump unit 13, a control unit etc.

Figure 3:
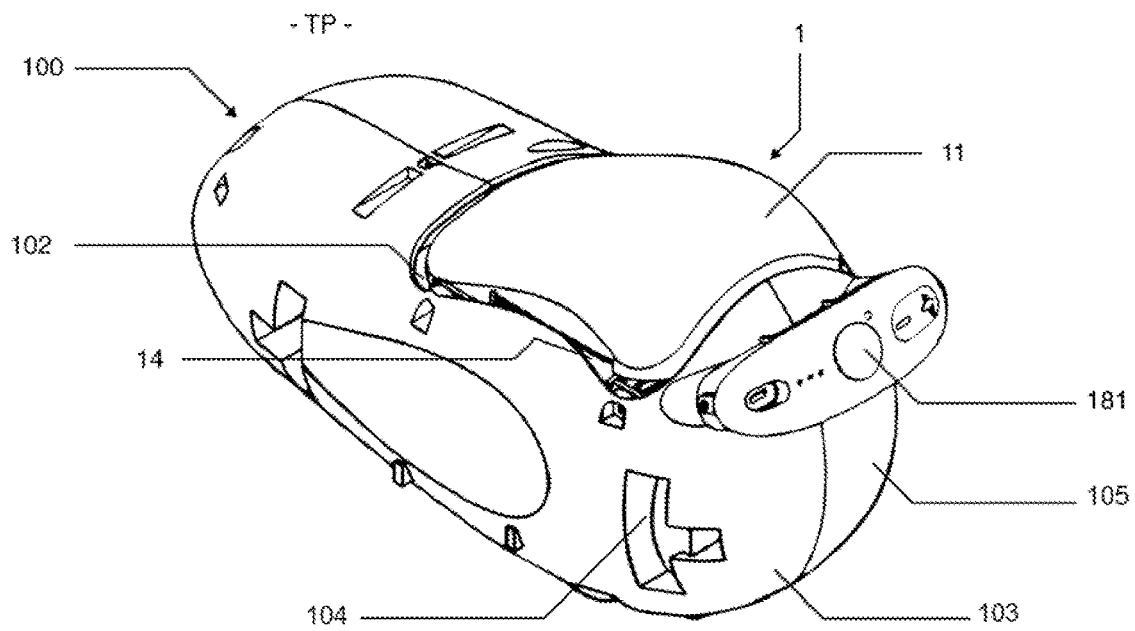
FIG. 3 shows a perspective view of the relaxation device of FIG. 1 without a cushion illustrating the breathing motion simulator positioned at an outer side of the housing.

The housing 101 is made of plastic. The housing 101 is manufactured by injection moulding. The housing 101 is formed by an outer shell 103 which forms a hard outer side of the housing. As shown in FIG. 3, the outer shell 103 has an upper and a lower half. The outer shell 103 comprises an upper shell section 104 and a lower shell section 105 whose outer contours fit to each other to enclose the inner space 109.

Here, the outer shell 103 of the housing 101 determines an outer shape of the relaxation monitoring device. The cushion 170 fully circumvents the outer shell 103. The outer shell 103 is configured to be covered by the foam body 171 of the cushion 170. The foam body is formed by a layer. The foam body 171 has a substantially constant thickness.

The relaxation monitoring device 100 comprises at least one sensor for monitoring a physiological characteristic of the user. The device may include a temperature sensor and/or an accelerometer as a sensor for measuring vibrations to deduct heart and/or respiration data.

Figure 13:
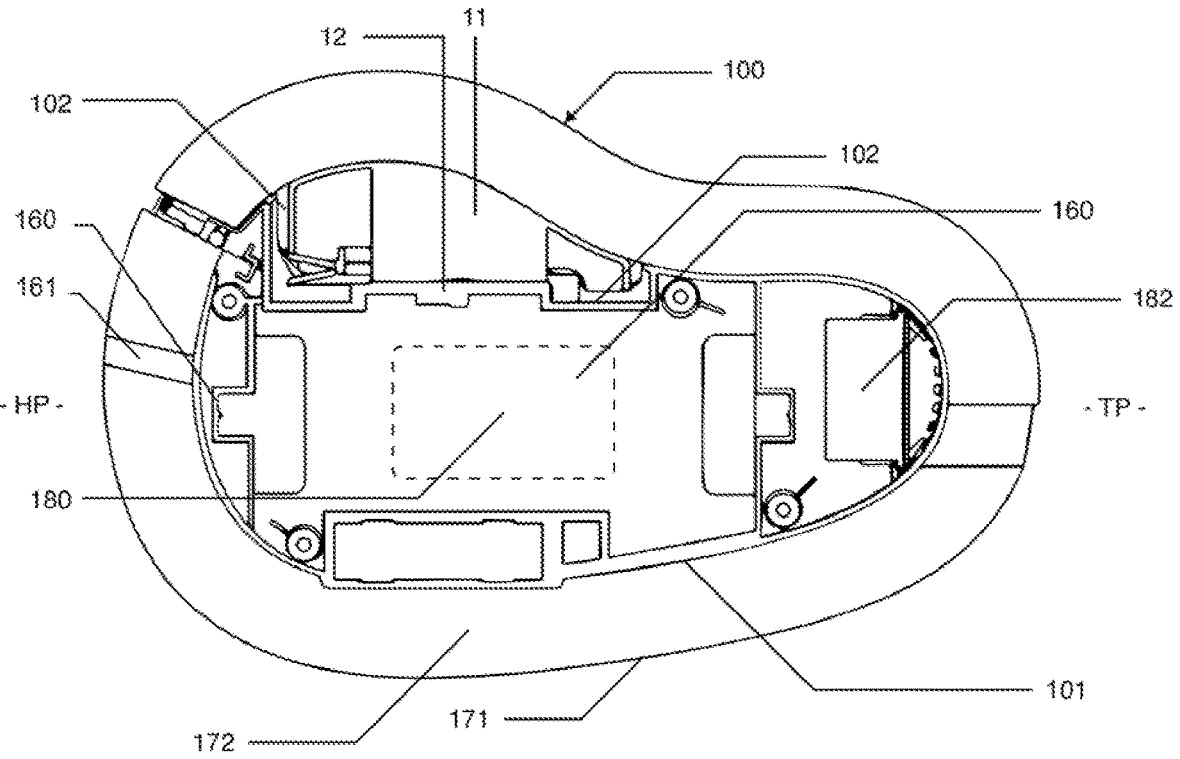

Particularly, as shown in FIG. 13, the at least one sensor may comprise a respiratory sensor 160 for measuring at least one characteristic of a gaseous medium in contact with the sensor. The respiratory sensor 160 is positioned at a head portion HP of the outer shape of the device 100. At least one air passageway 161 is positioned at the head portion HP to allow an airflow along the respiratory sensor. The respiratory sensor 160 may be a CO2 sensor for measuring a CO2 concentration in an exhaled air flow of the user.

The relaxation monitoring device 100 further comprises a control unit 180. Here, the control unit 180 is housed in the housing 101. The control unit 180 is connected to the at least one sensor 160 for receiving a sensor signal from the at least one sensor 160. The control unit 180 includes a printed circuit board. The sensor 160, here an accelerometer, is positioned on the printed circuit board. The relaxation monitoring device 100 is controlled by the control unit 180 based on a received sensor signal from the at least one sensor 160.

Here, the control unit 180 is electronically connected with a control panel 181. The control panel 181 is positioned at an outer side of the device. The control panel may include an on/off switch, display, LED etc.

Further, the relaxation monitoring device 100 may include a speaker 182. Here, the speaker is positioned at a tail portion TP of the device.

The relaxation device, here including at least one sensor 160 and configured as a relaxation monitoring device 100 for providing a relaxation stimulus based on at least one monitored physiological parameter, comprises a breathing motion simulator 1 according to the invention.

Figure 4:
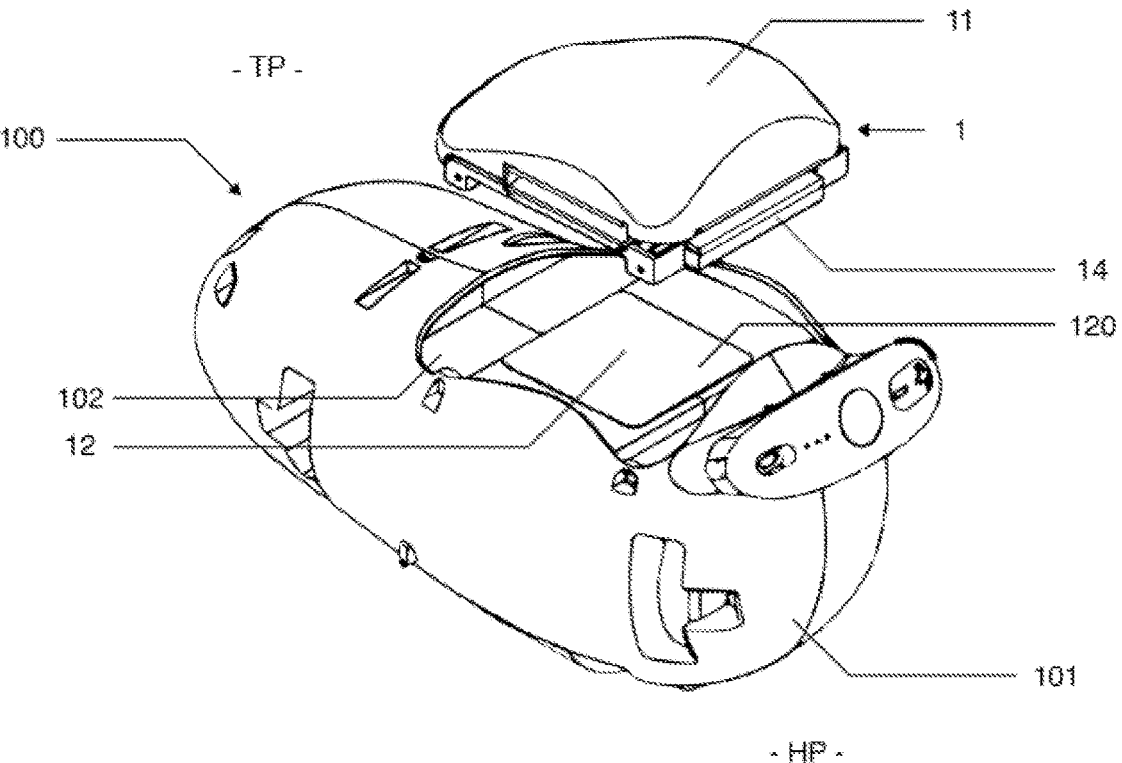
FIG. 4 shows an exploded view of the relaxation device of FIG. 3.

As shown in cross sectional view FIG. 2 and in a perspective view in FIGS. 3 and 4, the breathing motion simulator 1 is connected to the housing 101 which forms the base body 10. The housing 101 has a housing recess 102 for receiving the breathing motion simulator 1.

As shown in FIG. 2, the housing 101 of the relaxation monitoring device 100 can be considered as having a substantially two halves in length direction. The device has one half forming a head portion HP having a larger outer diameter than the other half forming a tail portion TP.

The breathing motion simulator 1 is positioned in the head portion HP of the relaxation monitoring device 100. In a longitudinal direction, the breathing motion simulator 1 extends across substantially the whole head portion HP. The breathing motion simulator 1 extends about a half a length of the relaxation monitoring device 100. In comparison with the relaxation monitoring device as disclosed in WO2020/162750, here a larger outer area of the device is moved during operation.

The breathing motion stimulator 1 comprises an actuator system which is here formed by a pump unit 13 which is fluidly connected to an inflatable bladder 12. The actuator formed by the inflatable bladder 12 is arranged for generating a repetitive motion. The frequency of the repetitive motion resembles a live breathing motion.

As shown in an exploded view in FIG. 4, the inflatable bladder 12 has a bladder body 120 which is positioned outside the housing 101. The bladder body is positioned in an abutting engagement with an outer surface of the housing 101. Here, the bladder body 120 is attached by gluing to the outer surface of the housing 101. The inflatable bladder 12 is configured to simulate a respiration motion by repeated inflation (expansion) and deflation (contraction) of the bladder 12. The inflation and deflation of the bladder 12 can be sensed by a user through the cushion 170 at an outside of the relaxation monitoring device 100.

The pump unit 13 is an actuator drive which is configured to inflate the inflatable bladder 12. The pump unit 13 includes a pump which is positioned inside the housing 101.

Here, the pump is a diaphragm pump. The pump has a pump outlet which is in fluid communication with a bladder inlet of the inflatable bladder 12.

Preferably, the inflatable bladder body 120 is of a permeable material, e.g. a porous material, so that the bladder body 120 automatically deflates without a need for an air suction. This may beneficially decrease the amount of components needed.

The breathing motion simulator 1 further comprises a cover plate 11. The cover plate 11 is positioned across the inflatable bladder 12. The cover plate 11 fully covers the bladder 12 underneath. Here, the cover plate 11 has a convex shaped. The cover plate 11 is shaped in correspondence with an inner shape of a human hand palm. A human hand can be ergonomically placed across the cover plate.

The cover plate 11 has a shape which is aligned with the shape of the housing 101. The shape of the cover plate 11 is incorporated in the shape of the relaxing monitoring device 100.

As shown in FIG. 2, the cover plate 11 extends in a length direction of the device 100 over a distance of at least 30%, in particular at least 40%, more in particular at least 50% of a total length of the device 100. Advantageously, a moving cover plate 11 generates a movement of a relative large outer surface area of the device 100 to be sensed by a user.

A cover guidance 14 is connected to the cover plate 11. The cover plate 11 is connected to an upper portion of the cover guidance 14. The cover guidance 14 has a bottom portion to be attached to the base body 10.

The cover guidance 14 is arranged for guiding the cover plate 11 with respect to the base body 10 formed by the housing 101. Due to the configuration of the cover guidance 14, the cover plate 11 is movable in only one degree of freedom (DOF) which is a translation. The cover guidance 14 only permits a linear movement of the cover plate.

Figure 5:
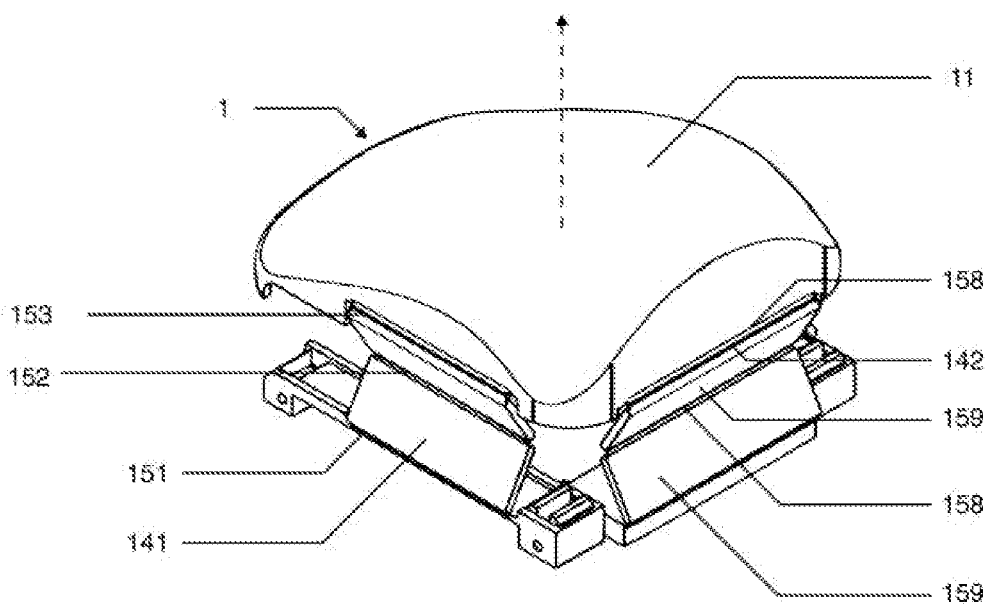
FIG. 5 schematically shows the breathing motion simulator including a bladder positioned below a cover plate guided by a cover guidance.
Figure 6:
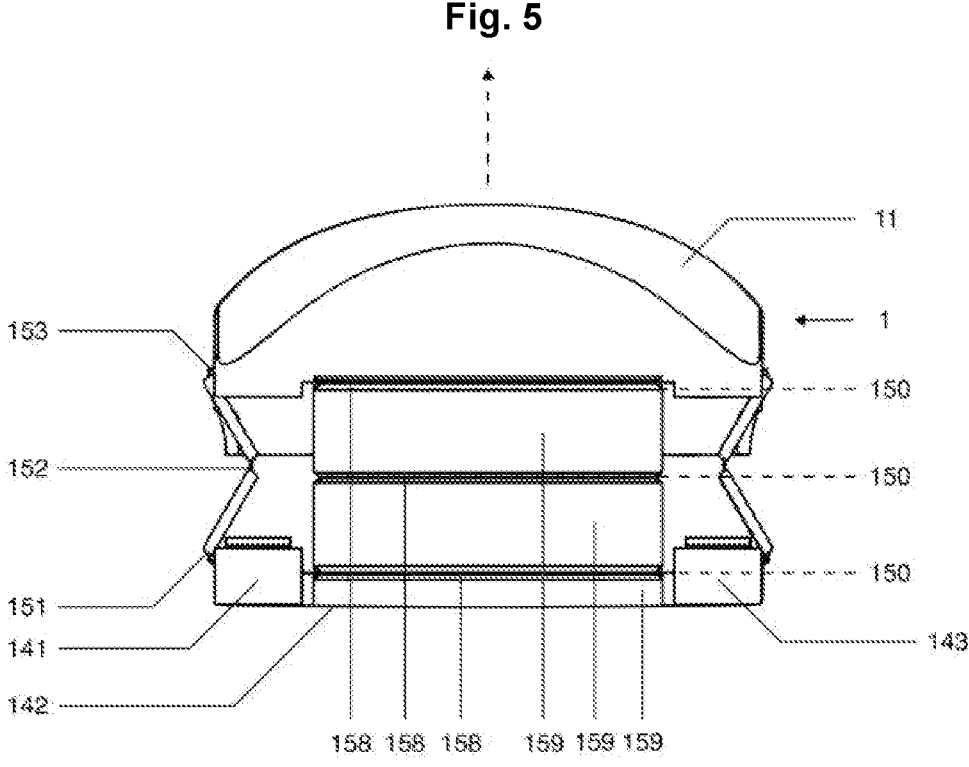
FIG. 6 shows a kinematic scheme of the cover guidance of FIG. 5.

As schematically shown in FIGS. 5 and 6, the cover guidance 14 comprises a set of living hinge units 140. A first, second and third living hinge unit 141, 142, 143 are provided. Each living hinge unit 140 is an integral item formed by injection moulding. The living hinge units are positioned along a circumference of the cover guidance 14. The bladder 12 is positioned in between the living hinge units.

Each living hinge unit has a same configuration. Each living hinge unit 14 includes a first, second and third living hinge 151, 152, 153.

In itself, a living hinge is a well-known mechanical design item. A living hinge extends in a longitudinal direction forming a pivot axis in between two rigid parts. A living hinge is formed by a linearly extending flexible section 158 positioned in between two rigid sections 159. The flexible section 158 defines the pivot axis 150.

In the living hinge unit 140, the living hinges 151, 152, 153 extend in parallel with each other. The pivot axes of the three living hinges are in parallel with each other. The three living hinges are stacked above each other. The first living hinge 151 is positioned at the bottom portion of the living hinge unit. The first living hinge 151 is connected to the base body 10. The third living hinge 153 is positioned at a top portion of the living hinge unit and connected to the cover plate 11. The second living hinge 152 is positioned between the first and third living hinge 151, 153. The second living hinge 152 interconnects the first and third living hinge. An embodiment is conceivable including more than one living hinge in between the top and bottom living hinge.

Herewith, in considering the degrees of freedom DOF's provided by the cover guidance 14, each individual living hinge unit 14 on itself allows a rotation and a translation with respect to the lowest living hinge at the base body 10. A combination of at least two living hinge units 140 oriented in a non-parallel direction constraints the freedom of rotation and permits a translation only of the cover plate 11. Here, three living hinge units 140 are combined to constrain five degrees of freedom to allow one freedom of movement of the cover plate 11 in translation.

Figure 7:
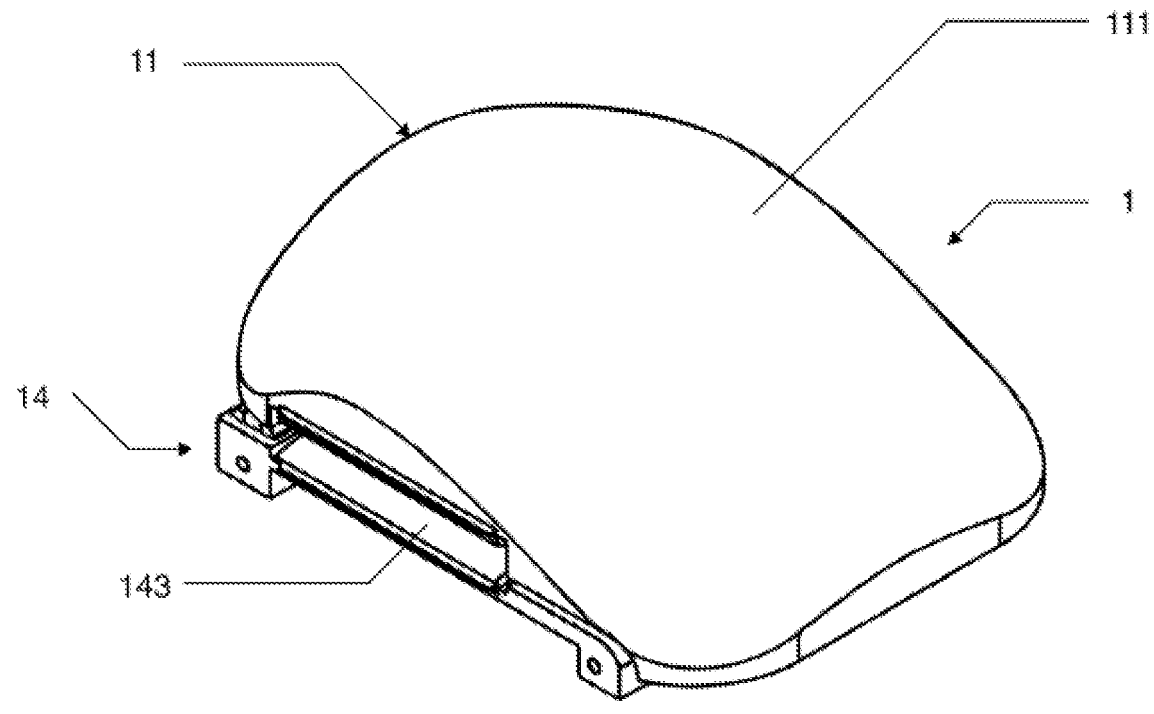
FIGS. 7-9 show in several views a subassembly of the cover plate and the cover guidance.
Figure 8:
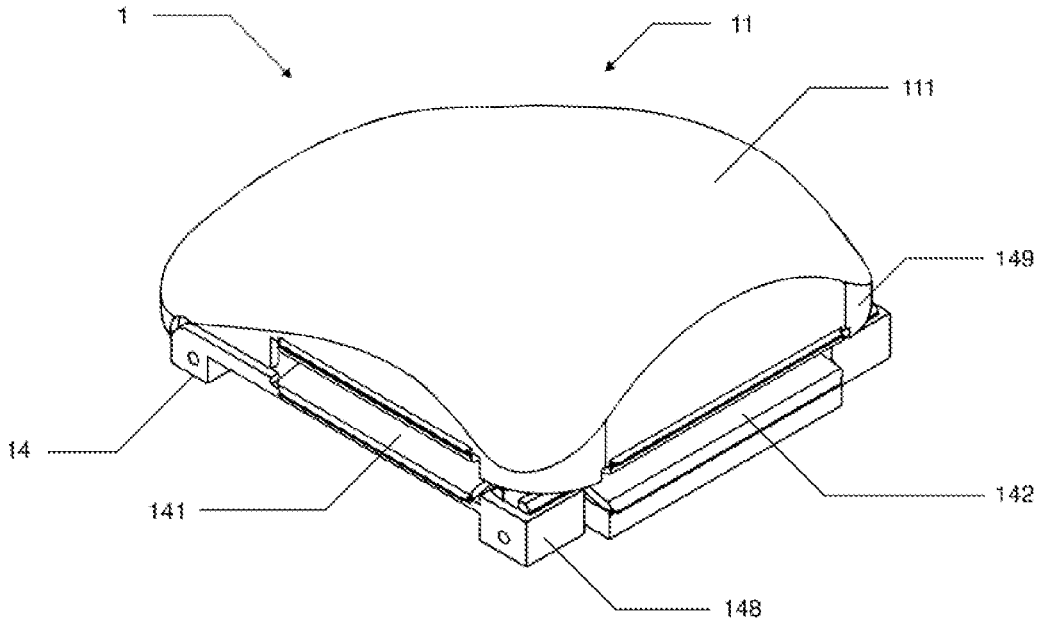
Figure 9:
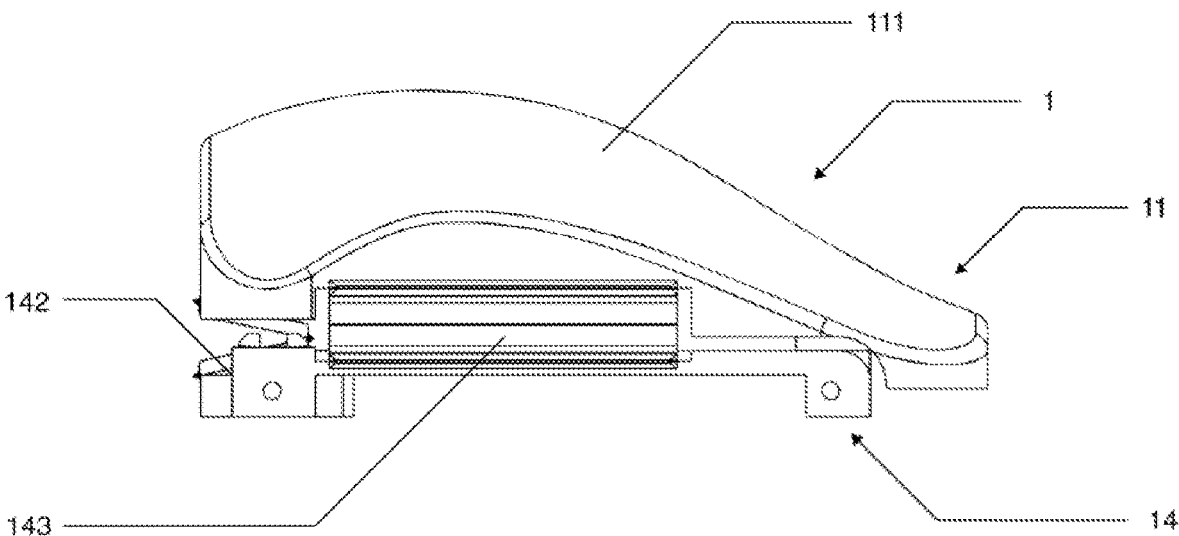

FIG. 7-9 show in several views a subassembly of the cover plate 11 and the cover guidance 14. The cover plate 11 is manufactured by injection moulding. The cover plate 11 has a concave outer surface 111. The cover plate has a substantially constant wall thickness. The cover guidance 14 has a first, second and third living hinge unit 141, 142, 143 which are positioned along a circumference of the cover plate 11. Here, the subassembly is shown in a collapsed configuration mountable to a base body.

The cover guidance 14 has a lower portion which is adapted to assemble the assembly to a base body 10.

Figure 10:
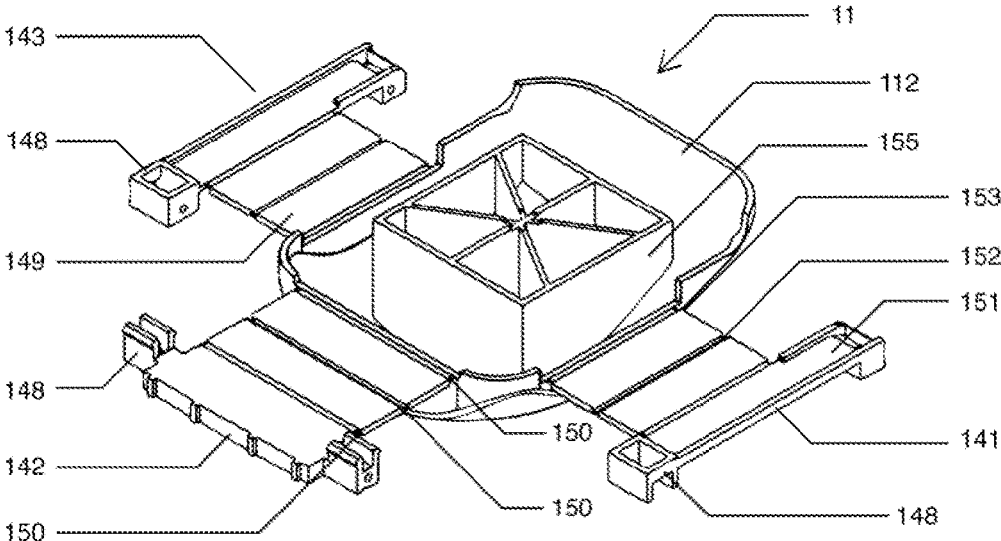
FIGS. 10 and 11 show respectively a perspective and bottom view of the subassembly as shown in FIGS. 7-9 including a push body to be engaged by the bladder of the breathing motion simulator.
Figure 11:
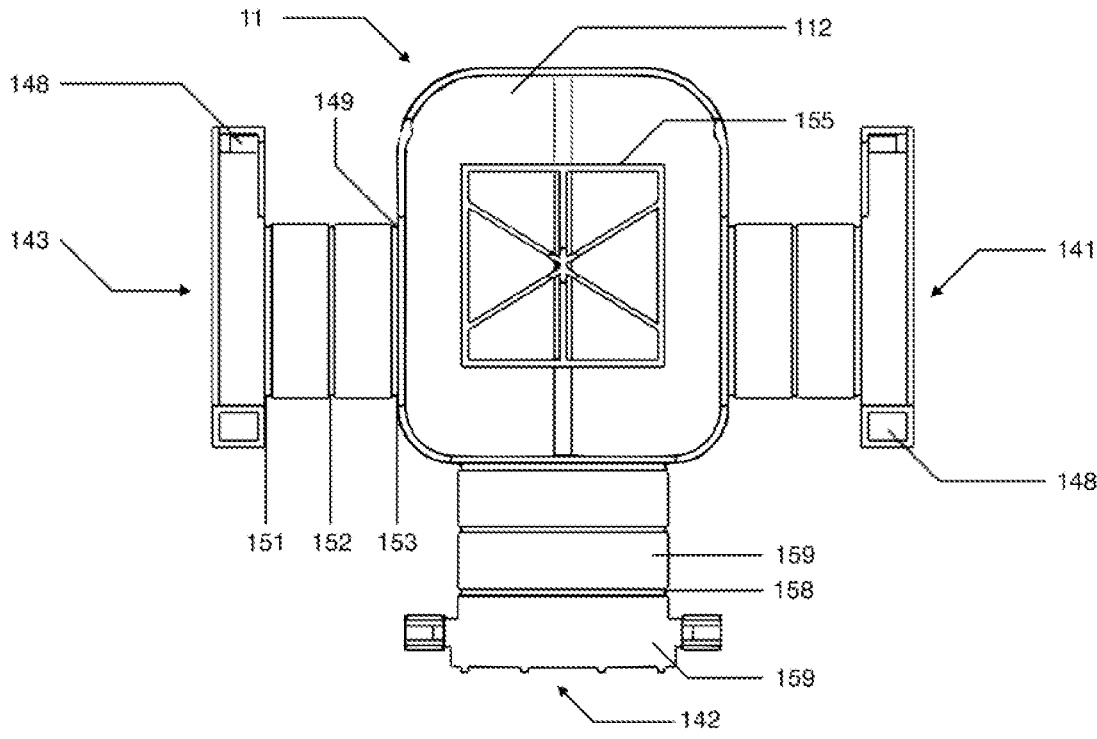

FIGS. 10 and 11 show the subassembly in further detail in which the living hinge units are shown in an unfolded configuration. The subassembly can be integrally manufactured by injection moulding in this unfolded configuration. After moulding, the living hinge units can be pivoted to obtain the collapsed configuration as shown in FIG. 7-9.

Preferably, as shown here, each living hinge unit 141, 142, 143 is separately manufactured by injection moulding, and thereafter coupled to the cover plate 11. The cover plate 11 may comprise a coupling member 113 at an inner surface 112, and the living hinge unit may comprise a complementary coupling member 144 at the upper portion 149 for coupling the living hinge unit to the cover plate 11. Here, the coupling member 113 is a snap connector formed by a protrusion and the living hinge unit includes a complementary aperture to snap the living hinge unit to the snap connector.

As shown, each living hinge unit has a bottom portion 148 which is adapted to connect the subassembly to the base body 10. The bottom portion 148 comprises a plurality of snap connectors to connect the subassembly to the base body.

The subassembly further comprises a push body 155. Here, the push body 155 is block-shaped. The push body 155 can be manufactured by injection moulding. The push body 155 is a hollow body comprising a plurality of thin-walled portions. The push body 155 comprises at least one push body connector to connect the push body 155 to the inner surface 112 of the cover plate 11. Here, the push body 155 is coupled by at least one snap connector to the cover plate, in particular by a plurality of snap connectors along an outer circumference of the push body 155.

Figure 12:
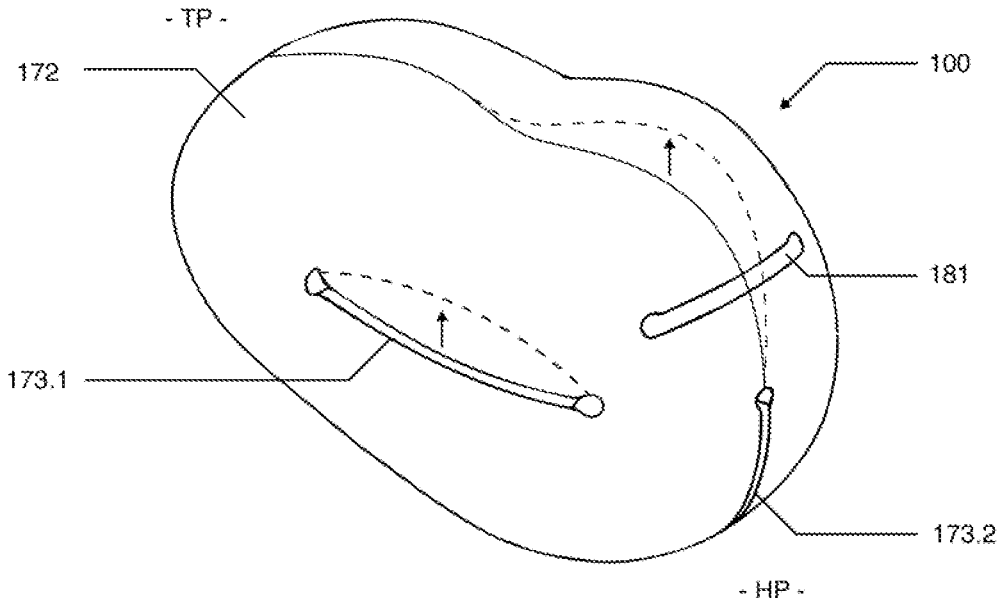
FIGS. 12 and 13 show respectively a perspective and cross-sectional view of the relaxation device as shown in FIGS. 2 and 3 provided with an enclosing cushion formed by a layer of foam provided with at least one cut-out.

FIGS. 12 and 13 show the relaxing monitoring device 100 as shown in FIGS. 2 and 3 including a foam body 172 of a cushion 170 which encloses the housing 101. The foam body 172 has an open worked region which here comprises a at least one cut-out 173. Here, the cut-out is formed by a first and second elongated groove 173.1, 173.2. The elongated groove 173 extends in a longitudinal direction in between the head portion HP and tail portion TP of the device.

The first elongated groove 173.1 is situated at a lateral side of the relaxation device. The second elongated groove 173.2 is situated at a bottom side of the relaxation device. As indicated by the arrow and the dashed line in FIG. 12, the breathing motion simulator 1 is situated at a top side of the relaxation device under a layer of foam material. The layer of foam material biases the subassembly of the cover plate 11 and the cover guidance 14. The layer of foam material provides a pre-tension. In operation, at the breathing motion simulator, the layer of foam material moves up and down, which generates a stretch of the foam material along a cross-sectional circumference of the foam body 172. The provided cut-outs 173 contribute in allowing the foam material to stretch and may prevent a rupture of the foam body 172.

Thus, the invention provides a breathing motion simulator for simulating an expanding and retracting movement of a live breathing, comprising a pump and an inflatable bladder for generating a repetitive motion resembling a breathing motion. The simulator comprises a cover plate positioned across the bladder and a cover guidance for linearly guiding the cover plate with respect to a base body. The cover guidance comprises at least a first living hinge unit and a second living hinge unit oriented in a non-parallel direction with respect to each other to provide a rotational constraint to the cover plate, wherein each living hinge unit comprises at least three stacked living hinges defining a set of three pivot axes in parallel for allowing a translational movement of the cover plate, such that the cover guidance enables a linear movement of the cover plate.

Although the present invention has been described in detail, it will be apparent to those skilled in the art that various changes and modifications can be made without departing from the scope of the invention as hereinafter claimed. It is intended that all such changes and modifications be encompassed within the scope of the present disclosure and claims.

LIST OF REFERENCE NUMBERS

P person; user
BP body part
1 breathing motion simulator; inflatable air chamber; air-pocket
10 base body
11 cover plate
111 outer surface
112 inner surface
113 coupling member
12 actuator; bladder
120 bladder body
13 actuator drive; pump unit
14 cover guidance
140 living hinge unit
141 first living hinge unit
142 second living hinge unit
143 third living hinge unit
144 coupling member
148 lower portion
149 upper portion
15 living hinge
151 first living hinge
152 second living hinge
153 third living hinge
150 pivot axis
155 push body
158 Flexible section
159 Rigid section
100 relaxation monitoring device
HP head portion
TP tail portion
101 housing
102 housing recess
103 outer shell
104 upper shell section
105 lower shell section

13

109 inner space
160 sensor
161 air passageway
170 cushion
171 pillow case
172 foam body
173 cut out; elongated groove
180 control unit
181 control panel
182 speaker
190 battery pack

We claim:

1. A breathing motion simulator for simulating an expanding and retracting movement of a breathing, comprising:
   an actuator system including an inflatable bladder and a pump unit including a pump for supplying a fluid to the inflatable bladder;
   a cover plate positioned across the inflatable bladder for covering the inflatable bladder to induce the motion of the inflatable bladder to the cover plate;
   a cover guidance for linearly guiding the cover plate with respect to a base body, in which the cover plate is connected to an upper portion of the cover guidance, and in which a lower portion of the cover guidance is connectable to the base body, wherein the cover guidance comprises at least a first living hinge unit and a second living hinge unit oriented in a non-parallel direction with respect to each other for constraining a rotational movement of the cover plate, wherein each living hinge unit comprises at least three stacked living hinges defining a set of at least three pivot axes in parallel for enabling a translational movement of the cover plate to allow that the cover guidance enables a linear movement of the cover plate.

2. The breathing motion simulator according to claim 1, wherein the cover guidance further comprises a third living hinge unit, wherein the third living hinge unit is oriented in parallel with the first living hinge unit.

3. The breathing motion simulator according to claim 1, wherein the second living hinge unit is oriented perpendicular to the first living hinge unit.

4. The breathing motion simulator according to claim 1, wherein the living hinge units are positioned along a circumference of the cover plate, and wherein the actuator is positioned in between the living hinge units.

5. The breathing motion simulator according to claim 1, wherein the cover guidance and the cover plate are integrally formed as a one piece item.

6. The breathing motion simulator according to claim 1, wherein the cover plate has an outer shape which is shaped in correspondence with a human hand palm.

7. The breathing motion simulator according to claim 1, wherein the cover plate comprises a push body to be engaged by the actuator, wherein the push body forms a protrusion extending away from an inner side of the cover plate.

8. The breathing motion simulator according to claim 7, wherein the push body is a hollow body formed by a plurality of wall portions having each a wall thickness allowing a manufacturing of the push body by injection molding.

9. The breathing motion simulator according to claim 7, wherein the push body is configured to be assembled to the inner side of the cover plate.

10. The breathing motion simulator according to claim 1, wherein a stretchable layer encloses the cover plate and provides a pre-tension to the cover plate with respect to the base body.

11. The breathing motion simulator according to claim 10, wherein the stretchable layer comprises an open-worked region contributing to a movement of the cover plate with respect to the base body.

12. The breathing motion simulator according to claim 11, wherein the open-worked region is formed by an elongated cut-out which is directed substantially perpendicular to the linear motion.

13. The breathing motion simulator according to claim 10, wherein the open worked region is laterally positioned with respect to the cover plate.

14. The breathing motion simulator according to claim 10, wherein the actuator is an inflatable bladder, such that after an inflation, the bladder deflates due to a pre-tension on the cover plate.

15. The breathing motion simulator according to claim 1, wherein the breathing motion simulator is a part of a relaxation device, a sleep induction device, or a relaxation monitoring device.

16. A breathing motion simulator for simulating an expanding and retracting movement of a breathing, comprising:
   an actuator system including an inflatable bladder and a pump unit including a pump for supplying a fluid to the inflatable bladder;
   a cover plate positioned across the inflatable bladder for covering the inflatable bladder to induce the motion of the inflatable bladder to the cover plate;
   a cover guidance for guiding the cover plate with respect to a base body, in which the cover plate is connected to an upper portion of the cover guidance, and in which a lower portion of the cover guidance is connectable to the base body, wherein the cover guidance comprises at least a living hinge unit comprising at least one living hinge defining a pivot axis extending in a longitudinal direction substantially in parallel with an imaginary plane formed by the base body to guide the cover plate to and fro the base body.

17. A relaxation device for influencing a relaxation of a user by providing a breathing motion simulation comprising:
   the breathing motion simulator according to claim 1, and
   a base body for connecting the breathing motion simulator,
   wherein the base body is formed by a housing in which the actuator drive is housed inside an inner space of the housing and wherein the cover guidance is connectable or connected to an outer surface of the housing.

18. The relaxation device according to claim 17, wherein the relaxation device is a relaxation monitoring device comprising at least one sensor for monitoring a relaxation of a user, in which a control unit is configured to adapt a simulation of a breathing motion provided by the breathing motion simulator based on a received sensor signal from the at least one sensor.

19. The relaxation device according to claim 17, wherein the cover plate of the breathing motion simulator extends in a length direction of the relaxation device, extending from a head portion to a tail portion, about a distance of at least 30% of a total length of the device.

20. A method for providing a simulation of a breathing motion, comprising:

utilizing the breathing motion simulator according to claim 1 for providing a simulation of a breathing motion.

\* \* \* \* \*